United States Patent
Spasojevic et al.

(10) Patent No.: US 10,399,575 B2
(45) Date of Patent: Sep. 3, 2019

(54) COGNITIVE LOAD DRIVING ASSISTANT

(71) Applicant: Harman International Industries, Incorporated, Stamford, CT (US)

(72) Inventors: Mirjana Spasojevic, Palo Alto, CA (US); Stefan Marti, Oakland, CA (US); Davide Di Censo, Oakland, CA (US); Jaime Elliot Nahman, Oakland, CA (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 8 days.

(21) Appl. No.: 15/541,458

(22) PCT Filed: Jan. 11, 2016

(86) PCT No.: PCT/US2016/012908
§ 371 (c)(1),
(2) Date: Jul. 3, 2017

(87) PCT Pub. No.: WO2016/115053
PCT Pub. Date: Jul. 21, 2016

(65) Prior Publication Data
US 2018/0009442 A1    Jan. 11, 2018

Related U.S. Application Data
(60) Provisional application No. 62/102,434, filed on Jan. 12, 2015.

(51) Int. Cl.
*B60K 28/02* (2006.01)
*B60K 28/06* (2006.01)
(Continued)

(52) U.S. Cl.
CPC ........ *B60W 50/0098* (2013.01); *A61B 3/112* (2013.01); *A61B 5/0205* (2013.01);
(Continued)

(58) Field of Classification Search
CPC ............. B60W 50/0098; B60W 50/14; B60W 2050/146; B60W 2540/02;
(Continued)

(56) References Cited

U.S. PATENT DOCUMENTS

| | | | | |
|---|---|---|---|---|
| 2007/0182529 A1* | 8/2007 | Dobler | ................... | B60K 28/06 340/438 |
| 2007/0219672 A1* | 9/2007 | Fehr | ...................... | B60W 40/08 701/1 |

(Continued)

FOREIGN PATENT DOCUMENTS

| | | | |
|---|---|---|---|
| EP | 1374773 A1 | | 1/2004 |
| JP | 2011118565 A | * | 6/2011 |

(Continued)

OTHER PUBLICATIONS

International Search Report and Written Opinion of the International Searching Authority for Application No. PCT/US2016/012908, dated Apr. 19, 2016, 10 pages.

*Primary Examiner* — Aaron L Troost
(74) *Attorney, Agent, or Firm* — Artegis Law Group, LLP (57) ABSTRACT

In one embodiment, a cognitive load driving assistant increases driving safety based on cognitive loads. In operation, the cognitive load driving assistant computes a current cognitive load of a driver based on sensor data. If the current cognitive load exceeds a threshold cognitive load, then the cognitive load driving assistant modifies the driving environment to reduce the cognitive load required to perform the primary driving task and/secondary task(s), such as texting via a cellular phone. The cognitive load driving assistant (Continued)

may modify the driving environment indirectly via sensory feedback to the driver or directly through reducing the complexity of the primary driving task and/or secondary tasks. In particular, if the driver is exhibiting elevated cognitive loads typically associated with distracted driving, then the cognitive load driving assistant modifies the driving environment to allow the driver to devote appropriate mental resources to the primary driving task, thereby increasing driving safety.

17 Claims, 5 Drawing Sheets

(51) Int. Cl.
| | |
|---|---|
| *G01C 21/36* | (2006.01) |
| *A61B 5/18* | (2006.01) |
| *A61B 5/024* | (2006.01) |
| *A61B 5/053* | (2006.01) |
| *G08G 1/0968* | (2006.01) |
| *B60W 50/00* | (2006.01) |
| *A61B 5/0205* | (2006.01) |
| *A61B 5/00* | (2006.01) |
| *A61B 3/11* | (2006.01) |
| *G08G 1/04* | (2006.01) |
| *G08G 1/16* | (2006.01) |
| *B60W 50/14* | (2012.01) |

(52) U.S. Cl.
CPC .............. *A61B 5/18* (2013.01); *A61B 5/4064* (2013.01); *A61B 5/6893* (2013.01); *B60K 28/02* (2013.01); *B60K 28/06* (2013.01); *B60K 28/066* (2013.01); *G01C 21/36* (2013.01); *G01C 21/3602* (2013.01); *G01C 21/3617* (2013.01); *G08G 1/096827* (2013.01); *G08G 1/096833* (2013.01); *A61B 5/02438* (2013.01); *A61B 5/0531* (2013.01); *B60K 2350/965* (2013.01); *B60K 2350/967* (2013.01); *B60W 50/14* (2013.01); *B60W 2050/146* (2013.01); *B60W 2420/42* (2013.01); *B60W 2540/02* (2013.01); *B60W 2540/22* (2013.01); *G08G 1/04* (2013.01); *G08G 1/096855* (2013.01); *G08G 1/167* (2013.01)

(58) Field of Classification Search
CPC .. B60W 2540/22; A61B 3/112; A61B 5/0205; A61B 5/18; A61B 5/4064; A61B 5/6893; A61B 5/02438; A61B 5/0531; B60K 28/02; B60K 28/06; B60K 28/066; B60K 2350/965; B60K 2350/967; G01C 21/36; G01C 21/3602; G01C 21/3617; G08G 1/096827; G08G 1/096833; G08G 1/096855; G08G 1/167; G08G 1/04
See application file for complete search history.

(56) References Cited

U.S. PATENT DOCUMENTS

| | | | |
|---|---|---|---|
| 2009/0171240 A1* | 7/2009 | Aguilar | A61B 3/112 |
| | | | 600/558 |
| 2012/0235819 A1* | 9/2012 | Watkins | A61B 5/18 |
| | | | 340/573.1 |
| 2016/0007935 A1* | 1/2016 | Hernandez | A61B 5/7278 |
| | | | 600/301 |

FOREIGN PATENT DOCUMENTS

| | | |
|---|---|---|
| WO | 2004/101306 A1 | 11/2004 |
| WO | 2007/106722 A2 | 9/2007 |

* cited by examiner

COGNITIVE LOAD DRIVING ASSISTANT

CROSS-REFERENCE TO RELATED APPLICATIONS

The present application is a national stage application of the international application titled, "COGNITIVE LOAD DRIVING ASSISTANT," filed on Jan. 11, 2016 and having application number PCT/US2016/012908, which claims the priority benefit of the U.S. Provisional Patent Application having Ser. No. 62/102,434, filed on Jan. 12, 2015. The subject matter of these related applications is hereby incorporated herein by reference.

BACKGROUND

Field of the Various Embodiments

The various embodiments relate generally to automotive systems and, more specifically, to a cognitive load driving assistant.

Description of the Related Art

Oftentimes, drivers fail to focus an appropriate amount of attention on the task of driving. For example, drivers may not adjust their focus to adequately address complex driving situations attributable to traffic, the manner in which others are driving, pedestrians, road conditions, weather conditions, volume of traffic, and the like. Further, drivers typically engage in multiple, secondary in-vehicle activities that divert their attention from the primary task of driving. Such secondary in-vehicle activities may include listening to loud music, participating in conversations, texting, soothing a crying child, and so forth.

"Distracted" driving attributable to complex driving situations and secondary in-vehicle activities increases the likelihood of collisions and accidents. For example, a driver who is driving on a winding road at night while talking with a passenger and operating an entertainment system is more likely to become involved in an automobile accident than a driver who is focused solely on the task of driving along a straight road during the day. Moreover, because using in-vehicle technologies while driving has become widespread, the frequency of injuries from accidents caused by distracted driving has increased. Some examples of prevalent in-vehicle technologies are navigation systems and entertainments systems.

In general, the three primary types of driver distractions are visual distractions, manual distractions, and cognitive distractions. Many adverse driving conditions and in-vehicle activities lead to multiple types of driver distractions. For example, texting is associated with a visual distraction that causes the driver to take his or her eyes off the road, a manual distraction that causes the driver to take his or her hands off the steering wheel, and a cognitive distraction that causes the driver to take his or her mind off the task of driving.

Because the impact of cognitive distractions on a driver is more difficult to assess than the impact of visual distractions and manual distractions, most drivers are oblivious to the amount of mental resources required to perform activities and tasks. As a result, drivers typically fail to modify the driving environment or their actions to reduce their cognitive load when their level of driver distraction becomes dangerously high.

As the foregoing illustrates, more effective techniques that enable drivers to better understand their levels of cognitive load while driving would be useful.

SUMMARY

One embodiment sets forth a computer-readable storage medium including instructions that, when executed by a processor, cause the processor to perform the steps of computing a current cognitive load associated with a driver while the driver is operating a vehicle based on data received via one or more sensors; determining that the current cognitive load exceeds a baseline cognitive load; and in response, causing one or more actions to occur that are intended to reduce the current cognitive load associated with the driver.

Further embodiments provide, among other things, a method and a system configured to implement the computer-readable storage medium set forth above.

At least one advantage of the disclosed techniques is that conveying cognitive load levels to drivers and/or adjusting vehicle behavior based on cognitive load levels may increase driver safety. In particular, if the driver is exhibiting elevated cognitive loads typically associated with distracted driving, then a cognitive load driving assistant may take action to reduce the complexity of the driving situation and/or the secondary tasks that the driver is performing, thereby allowing the driver to devote appropriate mental resources to the primary driving task.

BRIEF DESCRIPTION OF THE DRAWINGS

So that the manner in which the above recited features of the various embodiments can be understood in detail, a more particular description, briefly summarized above, may be had by reference to embodiments, some of which are illustrated in the appended drawings. It is to be noted, however, that the appended drawings illustrate only typical embodiments and are therefore not to be considered limiting in scope, for the various embodiments may admit to other equally effective embodiments.

DETAILED DESCRIPTION

In the following description, numerous specific details are set forth to provide a more thorough understanding of the various embodiments. However, it will be apparent to one of skill in the art that the various embodiments may be practiced without one or more of these specific details.

Vehicle Overview

Figure 1:
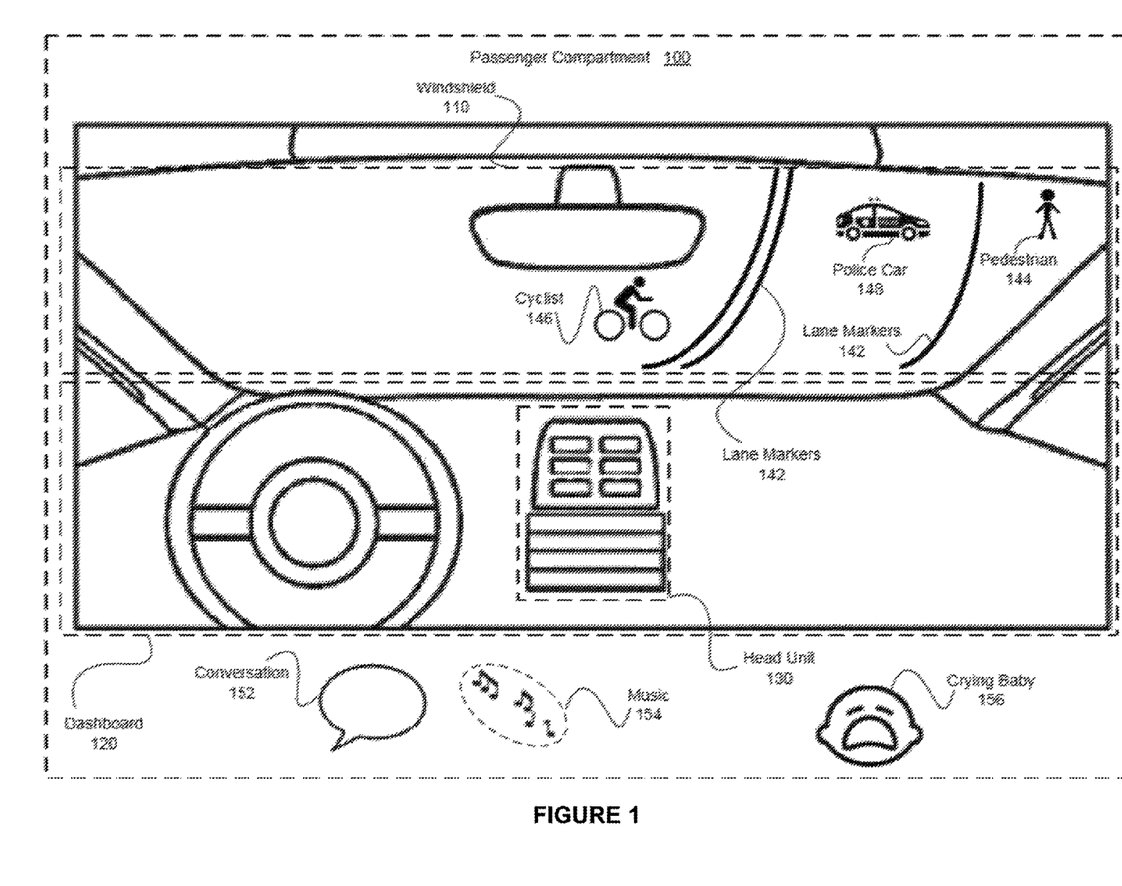
FIG. 1 illustrates a passenger compartment of a vehicle that is configured to implement one or more aspects of the various embodiments.

FIG. 1 illustrates a passenger compartment 100 of a vehicle that is configured to implement one or more aspects of the various embodiments. As shown, the passenger compartment 100 includes, without limitation, a windshield 110 and a head unit 130 positioned proximate to a dashboard 120. In various embodiments, the passenger compartment 100 may include any number of additional components that implement any technically feasible functionality. For example and without limitation, in some embodiments the passenger compartment 100 may include a rear-view camera.

As shown, the head unit 130 is located in the center of the dashboard 120. In various embodiments, the head unit 130 may be mounted at any location within the passenger compartment 100 in any technically feasible fashion that does not block the windshield 110. The head unit 130 may include any number and type of instrumentation and applications, and may provide any number of input and output mechanisms. For example, and without limitation, the head unit 130 typically enables the driver and/or passengers to control entertainment functionality. In some embodiments, the head unit 130 may include navigation functionality and/or advanced driver assistance functionality designed to increase driver safety, automate driving tasks, and the like.

The head unit 130 may support any number of input and output data types and formats as known in the art. For example, and without limitation, in some embodiments, the head unit 130 may include built-in Bluetooth for hands-free calling and audio streaming, universal serial bus (USB) connections, speech recognition, rear-view camera inputs, video outputs for any number and type of displays, and any number of audio outputs. In general, any number of sensors, displays, receivers, transmitters, etc. may be integrated into the head unit 130 or may be implemented externally to the head unit 130. External devices may communicate with the head unit 130 in any technically feasible fashion.

While driving, the driver of the vehicle is exposed to a variety of stimuli that are related to either the primary driving task and/or any number of secondary tasks. For example, and without limitation, the driver could see lane markers 142, a pedestrian 144, a cyclist 146, and a police car 148 via the windshield 110. In response, the driver could steer the vehicle to track the lane markers 142 while avoiding the pedestrian 144 and the cyclist 146 and apply the brake pedal to allow the police car 148 to cross the road in front of the vehicle. Further, and without limitation, the driver could concurrently participate in a conversation 152, listen to music 154, and attempt to soothe a crying baby 156. Challenging driving environments and secondary activities typically increase the cognitive load of the driver and may contribute to an unsafe driving environment for the driver and for objects (other vehicles, the pedestrian 144, etc.) in the proximity of the vehicle. In general, the head unit 130 includes functionality to enable the driver to efficiently perform both the primary driving task and certain secondary tasks as well as functionality designed to increase driver safety while performing such tasks.

Figure 2:
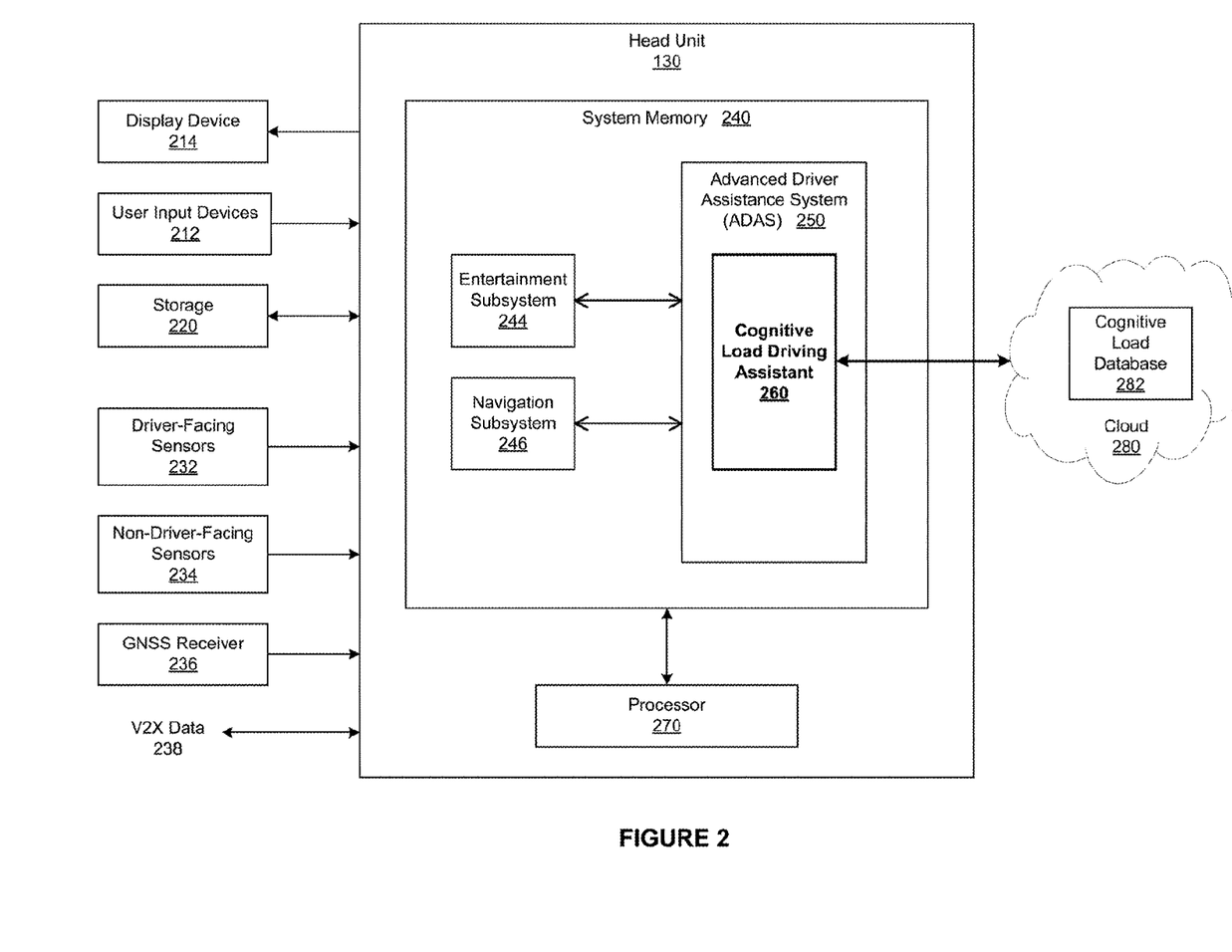
FIG. 2 is a more detailed illustration of the head unit of FIG. 1, according to various embodiments

FIG. 2 is a more detailed illustration of the head unit 130 of FIG. 1, according to various embodiments. As shown, the head unit 130 includes, without limitation, a processor 270 and a system memory 240. The processor 270 and the system memory 240 may be implemented in any technically feasible fashion. For example, and without limitation, in various embodiments, any combination of the processor 270 and the system memory 240 may be implemented as a stand-alone chip or as part of a more comprehensive solution that is implemented as an application-specific integrated circuit (ASIC) or a system-on-a-chip (SoC).

The processor 270 generally comprises a programmable processor that executes program instructions to manipulate input data. The processor 270 may include any number of processing cores, memories, and other modules for facilitating program execution. The processor 270 may receive input from drivers and/or passengers of the vehicle via any number of user input devices 212 and generate pixels for display on the display device 214. The user input devices 212 may include various types of input devices, such as buttons, a microphone, cameras, a touch-based input device integrated with a display device 214 (i.e., a touch screen), and other input devices for providing input data to the head unit 130.

The system memory 240 generally comprises storage chips such as random access memory (RAM) chips that store application programs and data for processing by the processor 270. In various embodiments, the system memory 240 includes non-volatile memory such as optical drives, magnetic drives, flash drives, or other storage. In some embodiments, a storage 220 may supplement or replace the system memory 240. The storage 220 may include any number and type of external memories that are accessible to the processor 170. For example, and without limitation, the storage 220 may include a Secure Digital Card, an external Flash memory, a portable compact disc read-only memory (CD-ROM), an optical storage device, a magnetic storage device, or any suitable combination of the foregoing.

As shown, the system memory 240 includes, without limitation, an entertainment subsystem 244, a navigation subsystem 246, and an advanced driver assistance system (ADAS) 250. The entertainment subsystem 244 includes software that controls any number and type of entertainment components, such as an AM/FM radio, a satellite radio, an audio and video computer files player (e.g., MP3 audio files player), an optical media player (e.g., compact disc (CD) player), and so forth. In some embodiments, any number of entertainment components may be included in the head unit 130 and any number of entertainment components may be implemented as stand-alone devices. The navigation subsystem 246 includes any number and type of applications that enable a driver to efficiently navigate the vehicle. For example, the navigation subsystem 246 may include maps, direction routing software, and the like.

The ADAS 250 includes functionality that is designed to increase driver safety and/or automate driving tasks. For example, and without limitation, in various embodiments, the ADAS 250 may provide hill descent control, automatic parking, and the like. Notably, the functionality included in the ADAS 250 may supplement, enhance, and/or automate functionality provided by other components included in the vehicle to decrease the likelihood of accidents or collisions in challenging conditions and/or driving scenarios.

In general, challenging driving environments and distractions may strain that ability of the driver to devote adequate attention to the primary driving task. For example, suppose that the driver is driving the vehicle during low light conditions along a congested, windy road while texting on a cell phone. In such a scenario, the driver may not devote enough mental resources to the primary driving task to operate the vehicle in a safe manner. However, many drivers do not recognize when their cognitive loads increase past a comfortable level and they begin to exhibit unsafe driving behaviors associated with distracted driving. For this reason, the ADAS 250 includes, without limitation, a cognitive load driving assistant 260.

Dynamically Modifying the Driving Environment Based on Cognitive Load

In general, the cognitive load driving assistant 260 continually estimates the current cognitive load of the driver and determines whether the current cognitive load indicates an abnormally stressful driving environment and/or an abnormal number of distractions. If the cognitive load driving assistant 260 determines that the current cognitive load indicates an abnormally stressful driving environment and/or an abnormal number of distractions, then the cognitive load driving assistant 260 attempts to indirectly or direct modify the driving environment to reduce the cognitive load of the driver. For example, and without limitation, the cognitive load driving assistant 260 could notify the driver of an atypically high cognitive load and suggest alternate driving routes that are less congested than the current driving route.

The cognitive load driving assistant 260 may process any type of input data and implement any technically feasible algorithm to estimate current cognitive load and/or determine whether the current cognitive load negatively impacts the driver's ability to safely operate the vehicle. As shown, and without limitation, the head unit 130, including the cognitive load driving assistant 260, receives data via any number of driver-facing sensors 232 and non-driver-facing sensors 234. The driver-facing sensors 232 may include devices capable of detecting and relaying physiological data associated with the driver. More specifically, the driver-facing sensors 232 may measure physiological change in the body related to cognitive load. In a complementary fashion, the non-driver-facing sensors 232 may include any devices capable of detecting and relaying that data that does not reflect the physiology of the driver but are related to the driving environment.

In general, the driver-facing sensors 232 and the non-driver-facing sensors 234 may include any type of sensors designed to measure any characteristic and may be implemented in any technically feasible fashion. In particular, the driver-facing sensors 232 may, without limitation, track specific features of the driver, such as hands, fingers, head, eye gaze, feet, facial expression, voice tone, and the like. For example, and without limitation, the driver-facing sensors 232 could include sensors that measure brain activity, heart rate, skin conductance, steering-wheel grip force, muscle activity, skin/body temperature, and so forth. Further, the driver-facing sensors 232 may include, without limitation, microphones that detect conversational context, conversational turn taking, voice tone and affect, other auditory distractions, and the like. For example, and without limitation, the driver-facing sensors 232 could detect that the driver is engaged in conversation with a passenger, the driver is currently speaking, the driver's voice tone indicates that the driver is drowsy, and two other passengers are engaged in a second conversation. In some embodiments, and without limitation, the driver-facing sensors 232 may include visual imagers that detect head position and orientation, facial features, hands movements, etc. In some embodiments, and without limitation, the driving facing sensors 232 may include depth sensors that detect finger and hand gestures, body posture, and as forth and/or eye gaze and pupil size tracking sensors.

In a complementary fashion, and without limitation, the non-driver-facing sensors 234 may track any features of the vehicle and/or environment surrounding the vehicle that are relevant to the driver. For example, and without limitation, the non-driver-facing sensors 234 may track vehicle control elements, such as the position of the throttle, the position of the clutch, gear selection, the location of the brake pedal, the angle of the steering wheel, and so forth. The non-driver-facing sensors 234 may include any number of sensors for tracking vehicle speed, position, orientation, and dynamics, such as inertial and magnetic sensors. Further, the non-driver-facing sensors 234 may include devices that detect and/or track stationary and/or moving objects surrounding the vehicle. Such detection sensors may include, without limitation, a front-mounted visible light imager, an infrared imager, a radio detection and ranging (RADAR) sensor, a light detection and ranging (LIDAR) sensor, a dedicated short range communication (DSRC) sensor, thermal and motion sensors, depth sensors, sonar and acoustic sensors, and the like. In some embodiments, and without limitation, the non-driver-facing sensors 234 may include remote sensors that provide information regarding local weather, traffic, etc.

The driver-facing sensors 232 and the non-driver-facing sensors 234 may be deployed in any technically feasible fashion. For example, and without limitation, the driver-facing sensors 232 and the non-driver-facing sensors 234 may include any number and combination of vehicle-integrated sensors, vehicle-integrated imagers, wearable devices (affixed to or worn by the driver), and remote sensors. In one example, and without limitation the, driver-facing sensors 232 could include steering wheel-mounted sensors that measure heart rate, skin conductance, and grip force, while the non-driver facing sensors 234 could include a front-mounted visible light imager, an infrared imager, and a LIDAR sensor.

In some embodiments, the cognitive load driving assistant 260 may receive additional input data, referred to herein as advanced driver assistance system (ADAS) data. Such ADAS data may include, without limitation, data received from a global navigation satellite system (GNSS) receiver 236, data received from the navigation subsystem 245, and data received from the entertainment subsystem 244. The global navigation satellite system (GNSS) receiver 236 determines global position of the vehicle. The GNSS receiver 236 operates based on one or more of the global positioning system of manmade Earth satellites, various electromagnetic spectrum signals (such as cellular tower signals, wireless internet signals, and the like), or other signals or measurements, and/or on a combination of the above items. In various embodiments, the cognitive load driving assistant 260 accesses global positioning data from GNSS receiver 236 in order to determine a current location of the vehicle. Further, in some embodiments, the cognitive load driving assistant 260 accesses data provided by the navigation subsystem 246 in order to determine a likely future location of the vehicle. In some embodiments, the cognitive load driving assistant 260 accesses data provided by entertainment subsystem 244 to assess the impact of secondary tasks, such as listening to music, on the cognitive load of the driver.

In yet other embodiments, the cognitive load driving assistant 260 may receive and transmit additional ADAS data including, and without limitation, automotive vehicle-to-everything (V2X) data 238. The vehicle-to-everything (V2X) data 238 may include vehicle-to-vehicle (V2V) data, vehicle-to-infrastructure (V2I) data, and so forth. The V2X data 238 enables the vehicle to communicate with other objects that include V2X capabilities. For example, the vehicle may communicate with other vehicles, smartphones, traffic lights, laptops, road-side V2X units, and so forth.

After receiving the input data, the cognitive load driving assistant 260 computes any number of cognitive metrics that relate to the current cognitive load of the driver. Subsequently, the cognitive load driving assistant 260 determines whether the cognitive metrics indicate that the driver may be unable to devote a typical and/or safe amount of mental resources to the primary task of driving. In general, the cognitive load driving assistant 260 may compute any number of cognitive metrics and assess whether the cognitive metrics indicate an elevated current cognitive load in any technically feasible fashion. For example, and without limitation, for a subset of the driver-facing sensors 232, the cognitive load driving assistant 260 could compute a current value for a cognitive metric and compare the current value to historical values for the cognitive metric. Substantially in parallel, for each of the remaining driver-facing sensors 232, the cognitive load driving assistant 260 could compare current sensor data to historical sensor data. The cognitive load driving assistant 260 could then determine whether the results of the various comparisons indicate an elevated current cognitive load.

For example, and without limitation, the cognitive load driving assistant 260 could compute a weighted average of the deviations of the values of any number of cognitive metrics and any number of driver-facing sensors 232 from historical values to determine an average deviation. If the average deviation exceeds a certain preset limit, then the cognitive load driving assistant 260 could determine that the current cognitive load is elevated. In another example, the cognitive load driving assistant 260 could compare the value of a primary cognitive load metric to historical values of the primary cognitive load metric to determine whether the current cognitive load may be elevated. Additionally, the cognitive load driving assistant 260 could compare the values of any number of driver-facing sensors 232 to historical values to provide a confidence measurement.

In general, the cognitive load driving assistant 260 may compute a current cognitive load based on any number, including one, of cognitive metrics and sensor data. Further, the cognitive load driving assistant 260 may determine historical values for cognitive metrics, cognitive loads, and/or sensor data in any technically feasible fashion. For example, and without limitation, in some embodiments the cognitive load driving assistant 260 may store the current cognitive load and other relevant data, referred to herein as a "driving context" in any available memory (e.g., the system memory 240). The driving context may include any number and type of data such as time of day, the location of the vehicle, detailed sensor readings, and so forth. Subsequently, the cognitive load driving assistant 260 may retrieve previously stored cognitive loads and driving contexts to determine historical cognitive loads at any level of situational granularity. For example and without limitation, in some embodiments, the cognitive load driving assistant 260 may compute an average cognitive load based on all historical cognitive loads. In other embodiments, and without limitation, the cognitive load driving assistant 260 may compute an average cognitive load based on the historical cognitive loads in similar driving contexts (e.g., the same time of day and/or location).

In some embodiments and without limitation, the cognitive load driving assistant 260 may transmit and/or receive cognitive loads and, optionally, driving contexts to other a cognitive load database 282 that is included in a cloud 280 (e.g., encapsulated shared resources, software, data, etc.). The cognitive load driving assistant 260 and other cognitive load driving assistants included in other vehicles may then retrieve information from the cognitive load database 282. The cognitive load driving assistant 260 may analyze such data as part of evaluating the current cognitive load, detecting situations that involve high cognitive loads, and so forth.

In some embodiments, the cognitive load driving assistant 260 may transmit and/or receive cognitive loads and, optionally, driving contexts with other cognitive load driving assistants 260 as V2X data 238. In general, the cognitive load driving assistant 260 may be configured to transmit and store data relevant to the cognitive load of the driver in any technically feasible fashion. Similarly, the cognitive load driving assistant 260 may be configured to receive and process data relevant to the cognitive loads of other drivers as well as any additional factors that may influence the cognitive load of the other drivers in any technically feasible fashion.

After determining the current cognitive load of the driver and assessing other relevant data, the cognitive load driving assistant 260 may perform any number of actions designed to increase the safety of the driver. As previously detailed, such relevant data may include, without limitation, such current location of the vehicle, time of day, data provided by the navigation subsystem 246 and the entertainment subsystem 244, cognitive loads of drivers along the planned driving route, and so forth. The actions may directly or indirectly modify the driving task and any secondary tasks that may distract the driver.

For example, and without limitation, the cognitive load driving assistant 260 could provide feedback to the driver via the display device 214. The feedback could include the current cognitive load, historical cognitive loads, and suggestions for reducing the complexity of the primary driving task, such as easier (less congested) driving routes or lanes. In some embodiments, and without limitation, the cognitive load driving assistant 260 may reduce human machine interface (HMI) complexity to reduce distractions. For example, and without limitation, the cognitive load driving assistant 260 could block incoming cellular phone calls, lower the volume of music, block non-critical alerts (e.g., low windshield washer fluid alert, etc.), and the like.

In some embodiments, the cognitive load driving assistant 260 may perform actions designed to preemptively increase driving safety. For example, and without limitation, suppose that the cognitive load driving assistant 260 detects elevated cognitive loads associated with other drivers in the proximately of the vehicle or along the driving route specified by the navigation subsystem 246. To increase the vigilance of the driver, the cognitive load driving assistant 260 may alert the driver to expect potentially hazardous situations (e.g., accidents, dangerous curves, etc.) and/or distracted drivers.

In some embodiments and without limitation, the cognitive load driving assistant 260 may work in conjunction with the navigation subsystem 246 and/or other elements included in the ADAS 250 to increase driving safety based on one or more predictive heuristics. In some embodiments, the cognitive load driving assistant 260 could configure the navigation subsystem 246 to avoid locations associated with elevated cognitive loads. For example, and without limitation, if elevated historical cognitive loads are associated with a particular exit to an airport, then the cognitive load driving assistant 260 could configure the navigation subsystem 246 to preferentially select an alternative exit to the airport. In other embodiments, upon detecting elevated cognitive loads of the driver or nearby drivers, the cognitive load driving assistant 260 could modify one or more ADAS parameters to increase the conservatism of the ADAS 250. For example, and without limitation, the cognitive load driving assistant 260 could configure preemptive braking to activate at an earlier time or could decrease the baseline at which the ADAS 250 notifies the driver of a lane departure from the current driving lane.

The cognitive load driving assistant 260 may configure the vehicle to provide feedback to the driver in any technically feasible fashion. For example, and without limitation, the cognitive load driving assistant 260 may configure the vehicle to provide any combination of visual feedback, auditory feedback, haptic vibrational feedback, tactile feedback, force feedback, proprioceptive sensory feedback, and so forth. Further, the cognitive load driving assistant 260 may configure any features of the vehicle in any technically feasible fashion. For example, the cognitive load driving assistant 260 may configure the entertainment subsystem 244, the navigation subsystem 246, applications included in the ADAS 250, and any control mechanisms provided by the vehicle via any number of control signals or via any type of interface.

As described above, in some embodiments the cognitive load driving assistant 260 receives cognitive load data and/or related data from other vehicles (e.g., via the cognitive load database 282, the V2X data 282, etc.). In operation, the cognitive load driving assistant 260 may leverage such shared data in any technically feasible fashion to optimize driving safety either at the current time or at a future time. For example, and without limitation, instead of comparing the current cognitive load to a personalized average cognitive load, the cognitive load driving assistant 260 could compare the current cognitive load to a baseline cognitive load based on collective cognitive loads of many drivers normalized for time, location, and other factors. In general, the cognitive load driving assistant 260 attempts to maintain the current cognitive load below the threshold represented by the baseline cognitive load.

In another example, and without limitation, the cognitive load driving assistant 260 may examine the average cognitive load of drivers in close proximity to the vehicle or along a driving route associated with the vehicle to detect a preponderance of elevated cognitive loads that indicates a complex situation, such as an accident. Upon detecting such an area of elevated cognitive loads, the cognitive load driving assistant 260 may generate a sensory warning designed to cause the driver to become more vigilant, generate a new driving route that avoids areas of elevated cognitive load, and so forth. In yet another example, and without limitation, the cognitive load driving assistant 260 may generate a "heat map" based on collective cognitive loads. The cognitive load driving assistant 260 may then suggest altering the driving environment based on the heat map. In particular, the cognitive load driving assistant 260 may recommend lane changes to lanes associated with lower cognitive loads; interact with the navigation subsystem 246 to optimize the driving route, and the like.

In general, the cognitive load driving assistant 260 may be configured to process any type of input data and/or compute any number of metrics related to cognitive load. Further, the cognitive load driving assistant 260 may be configured to increase driving safety and/or improve the driving experience based on the processed data and metrics in any technically feasible fashion. Although the cognitive load driving assistant 260 is described in the context of the head unit 130 herein, the functionality included in cognitive load driving assistant 260 may be implemented in any technically feasible fashion and in any combination of software and hardware. For example, and without limitation, each of the processor 270 and the system memory 240 may be embedded in or mounted on a laptop, a tablet, a smartphone, a smartwatch, a smart wearable, or the like that implements the cognitive load driving assistant 260. In other embodiments, and without limitation, the cognitive load driving assistant 260 may be implemented as a stand-alone unit that supplements the functionality of existing vehicle safety systems. Such a stand-alone unit may be implemented as a software application that executes on any processor.

Figure 3:
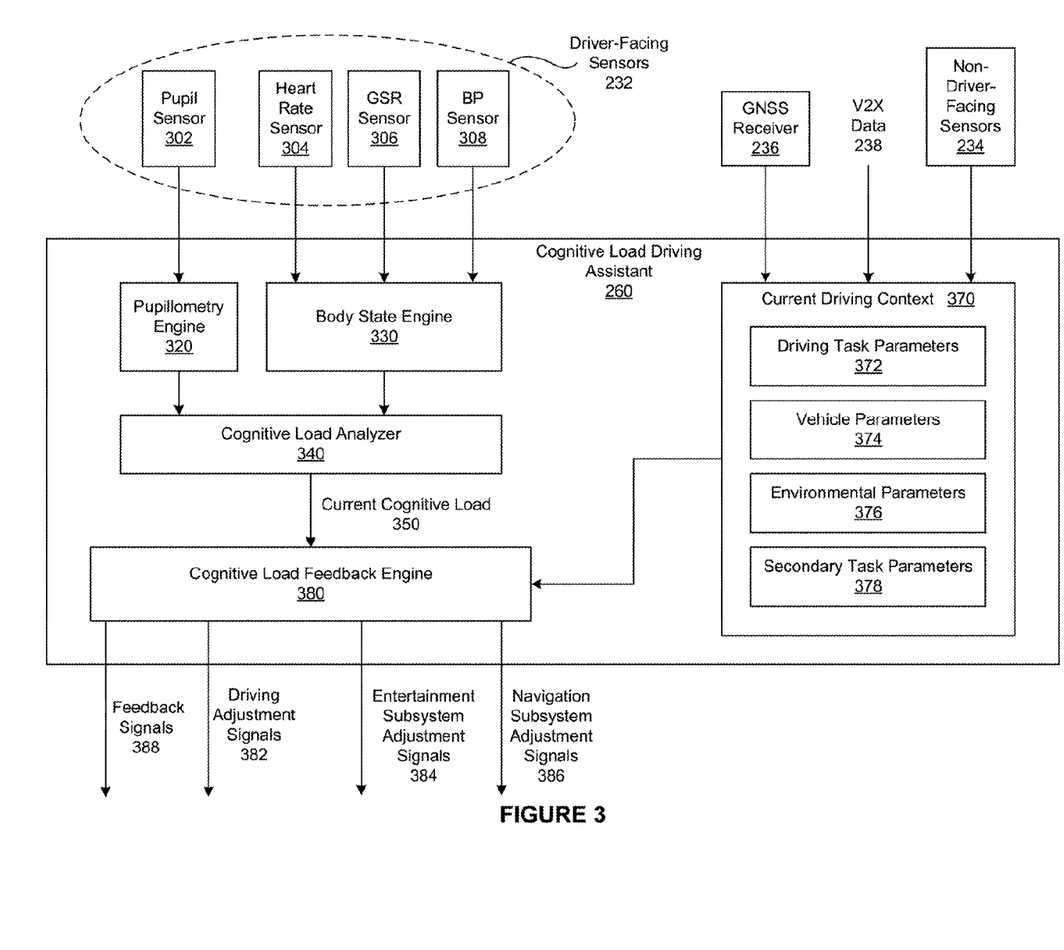
FIG. 3 is a more detailed illustration of the cognitive load driving assistant of FIG. 2, according to various embodiments.

FIG. 3 is a more detailed illustration of the cognitive load driving assistant 260 of FIG. 2, according to various embodiments. As shown, the cognitive load driving assistant 260 includes, without limitation, a pupillometry engine 320, a body state engine 330, a cognitive load analyzer 340, a current driving context 370, and a cognitive load feedback engine 380. In alternate embodiments and without limitation, any number of components may provide the functionality included in the cognitive load driving assistant 260 and each of the components may be implemented in software, hardware, or any combination of software and hardware.

In operation, the pupillometry engine 320 receives pupil data from a pupil sensor 302 that measures the sizes of the driver's pupils via eye tracking tools. Based on the pupil data, the pupillometry engine 320 computes a pupil-based metric that reflects the cognitive load of the driver. The pupillometry engine 320 may compute the pupil-based metric in any technically feasible fashion. For example, and without limitation, the pupillometry engine 320 may analyze the pupil data to identify specific rapid changes in pupil size that are associated with increased cognitive load.

Operating substantially in parallel to the pupillometry engine 320, the body state engine 330 receives sensor data from a heart rate sensor 304, a galvanic skin response (GSR) sensor 306, and a blood pressure (BP) sensor 308. Based on the sensor data, the body state engine 330 computes a body-based metric that reflects the cognitive load of the driver. The body state engine 330 may compute the body-based metric in any technically feasible fashion. For example, and without limitation, the body state engine 330 may evaluate the heart rate in conjunction with the skin rate to determine a level of psychophysiological arousal. Further, the body state engine 330 may evaluate the BP to estimate an amount of blood flow in the front part of the brain. In general, the body state engine 330 may evaluate any type of sensor data in any combination to compute any number of metrics that reflect the cognitive load of the driver.

As shown, the cognitive load analyzer 340 receives the pupil-based metric and the body-based metric and computes a current cognitive load 350 that approximates the cognitive load of the driver. The cognitive load analyzer 340 may compute the current cognitive load 350 in any technically feasible fashion. For example, and without limitation, the cognitive load analyzer 340 may compute the current cognitive load 350 as a weighted average of the pupil-based metric and the body-based metric. In various embodiments, the cognitive load analyzer 340 may perform any number of comparison operations between the current value of any number of metrics and any number and type of corresponding baseline values to determine the current cognitive load 350. Further, the cognitive load analyzer 340 may determine that the value of a particular metric is erroneous based on the values of other metrics. In some embodiments, the cognitive load analyzer 340 may compute the current cognitive load 350 based on a subset of metrics and compute a confidence value based on a different subset of metrics.

While the cognitive load driving assistant 260 evaluates data received via the driver-facing sensors 232, the cognitive load driving assistant 260 also generates a current driving context 370 that includes data received via the non-driver-facing sensors 234, data received via the GNSS receiver 236, and the V2X data 238. The current driving context 370 described the current driving environment. As shown, the current driving context 370 includes, without limitation, driving task parameters 372, secondary task parameters 378, vehicle parameters 374, and environmental parameters 376. In general, the driving task parameters 374 directly influence a driving task load that represents the mental resources required to perform the primary driving task. By contrast, the secondary task parameters 460 directly influence a secondary task load that represents the mental resources required to perform secondary tasks, such as operating the entertainment subsystem 244 or talking on a cellular phone. The vehicle parameters 374 and the environmental parameters 376 reflect circumstances that impact the mental resources required to perform the driving task and/or the secondary tasks. For example, and without limitation, the vehicle parameters 374 and the environmental parameters 376 could include the location of the vehicle, the condition of the road, the weather, the lighting conditions, and so forth.

As shown, the cognitive load feedback engine 380 receives the current cognitive load 350 and the current driving context 370 and generates, without limitation, feedback signals 388, driving adjustment signals 382, entertainment subsystem adjustment signals 384, and navigation subsystem adjustment signals 386. In operation, the cognitive load feedback engine 380 evaluates the current cognitive load 350 relative to a baseline cognitive load to determine whether the current cognitive load 350 is elevated. The cognitive load feedback engine 380 may determine the baseline cognitive load in any technically feasible fashion. For example, and without limitation, the baseline cognitive load could be a predetermined constant value. In some embodiments, the cognitive load feedback engine 380 may dynamically compute the baseline cognitive load based on any number and type of historical data associated with any number of drivers and any number of driving contexts.

If the cognitive load feedback engine 380 determines that the current cognitive load 350 is elevated relative to the baseline cognitive load, then the cognitive load feedback engine 380 may endeavor to reduce the current cognitive load 350. Notably, the cognitive load feedback engine 380 may examine the current driving context 370 to determine how to optimize the driving environment to reduce the driving task load and/or the secondary tasks loads. In general, the cognitive load feedback engine 380 may generate any number of control signals in any technically feasible fashion that is consistent with the capabilities and interfaces implemented in the vehicle. Such control signals may provide, without limitation, any combination of visual feedback, auditory feedback, haptic vibrational feedback, tactile feedback, force feedback, proprioceptive sensory feedback, and so forth.

For example, and without limitation, the cognitive load feedback engine 380 could transmit the feedback signals 388 that configure the display device 214 to provide visual feedback regarding the current cognitive load 350, historical cognitive loads, and recommendations for reducing the driving task and/or secondary tasks loads. If the vehicle is equipped with the advanced driving features, then the cognitive load feedback engine 380 could increase the conservatism of the vehicle via the driving adjustment signals 382, such as decreasing a baseline at which the ADAS 250 notifies the driver of a lane departure. In some embodiments, the cognitive load feedback engine 380 may configure the entertainment subsystem 244 via the entertainment subsystem adjustment signals 384 to reduce distractions associated with an in-vehicle audio system. In yet other embodiments, the cognitive load feedback engine 380 may configure the navigation subsystem 246 via the navigation subsystem adjustment signals 386 to replace a current driving route with a new driving route that is less congested, thereby lowering the mental resources required to perform the primary driving task.

Figure 4:
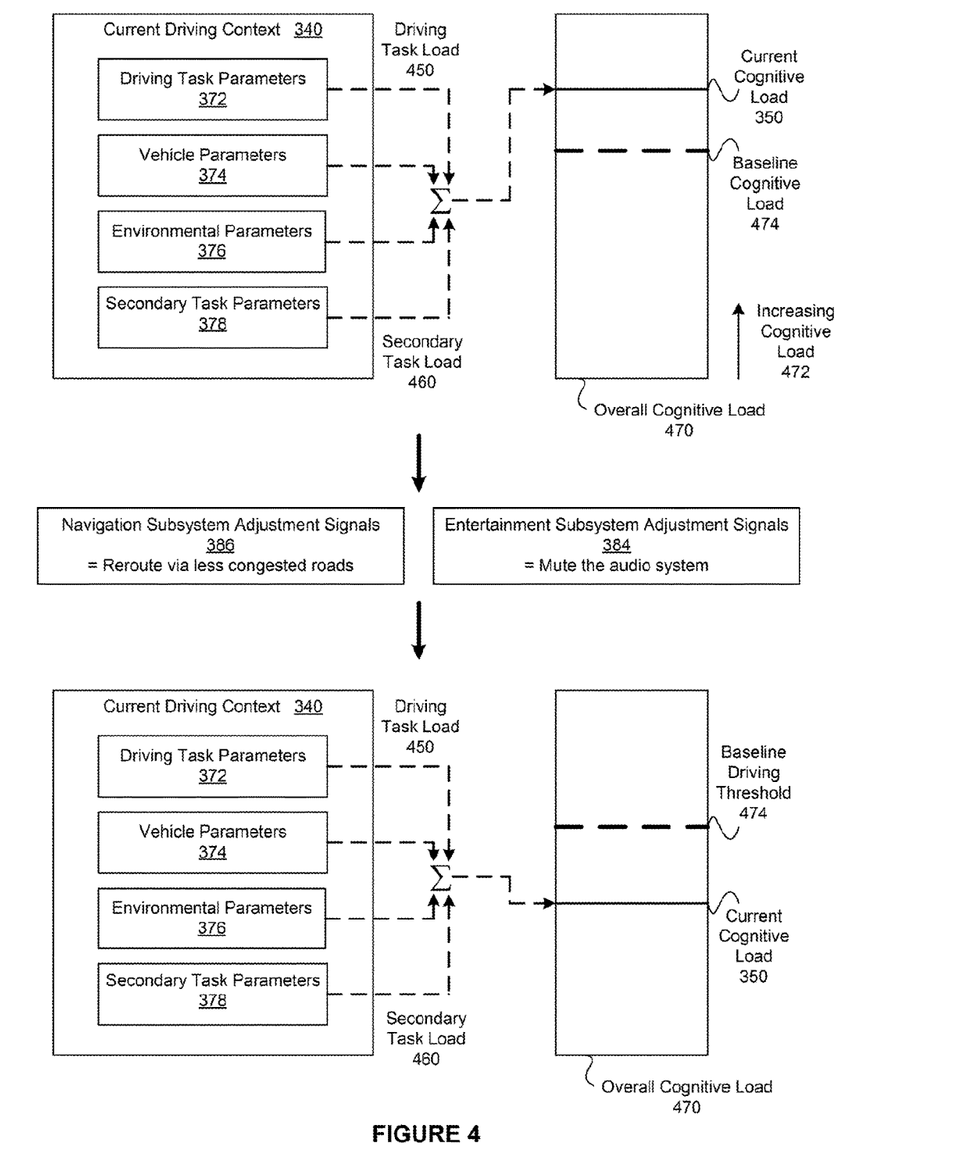
FIG. 4 illustrates the relationship between the current driving context and the current cognitive load of FIG. 3, according to various embodiments.

FIG. 4 illustrates the relationship between the current driving context 340 and the current cognitive load 350 of FIG. 3, according to various embodiments. As shown, the current driving context 340 includes the driving task parameters 372, the secondary task parameters 378, the vehicle parameters 374, and the environmental parameters 376. In general, the driving task parameters 372 directly influence a driving task load 450 that represents the mental resources required to perform the primary driving task. By contrast, the secondary task parameters 460 directly influence a secondary task load 460 that represents the mental resources required to perform secondary tasks, such as talking on a cell phone.

Together, the driving task parameters 372, secondary task parameters 378, vehicle parameters 374, and environmental parameters 376 contribute to the current cognitive load 350. In particular, as the driving task load 450 and/or the secondary task load 460 increases, the current cognitive load 350 increases (depicted as an increasing cognitive load 472) within an overall cognitive load 470. The overall cognitive load 470 represents the total cognitive load of the driver and, within the overall cognitive load 470, a baseline cognitive load 474 reflects the typical cognitive loads of the driver.

As shown, initially the current cognitive load 350 exceeds the baseline cognitive load 474. In response, the cognitive load feedback engine 380 analyzes the current driving context 370 and transmits the navigation subsystem adjustment signal 386 "reroute via less congested roads" to the navigation subsystem 246, and the entertainment subsystem adjustment signal 384 "mute the audio system" to the entertainment subsystem 244. Subsequently, as a result of the reduction in the driving task load 450 and the secondary task load 460 attributable to, respectively, the navigation subsystem adjustment signal 386 and the entertainment subsystem adjustment signal 384, the current cognitive load 350 decreases and no longer exceeds the baseline cognitive load 474.

As the foregoing example illustrates, in general, if the current cognitive load 350 exceeds the baseline cognitive load 474, then the cognitive load feedback engine 380 attempts to adjust the current driving context 340 to either directly or indirectly reduce the current cognitive load 350. Accordingly, the level of driver distraction is reduced and the safety of the driver and surrounding drivers is increased.

Figure 5:
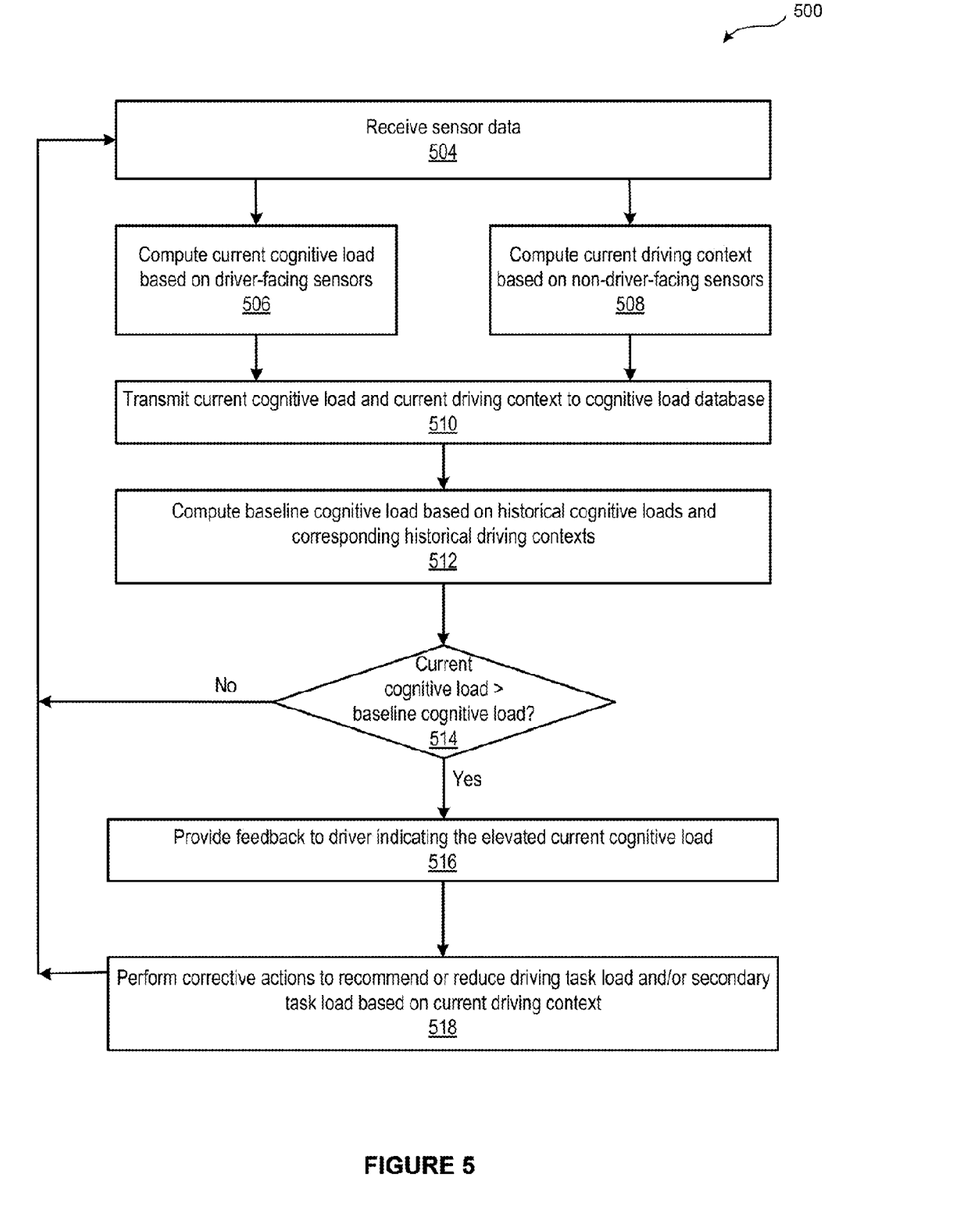
FIG. 5 is a flow diagram of method steps for managing cognitive load while driving, according to various embodiments.

FIG. 5 is a flow diagram of method steps for managing cognitive load while driving, according to various embodiments. Although the method steps are described in conjunction with the systems of FIGS. 1-4, persons skilled in the art will understand that any system configured to implement the method steps, in any order, falls within the scope of the various embodiments.

As shown, a method 500 begins at step 504, where the cognitive load driving assistant 260 included in a vehicle receives sensor data via the driver-facing sensors 232 and the non-driver-facing sensors 234. The driver-facing sensors 232 may include any number of sensors that monitor characteristics of the driver. For example and without limitation, the driver-facing sensors 232 may include the pupil sensor 302, the heart rate sensor 304, the galvanic skin response (GSR) sensor 306, the blood pressure (BP) sensor 308, and the like. By contrast, the non-driver-facing sensors 324 monitor data that is not directly related to the driver, such as environmental data and vehicle data.

At step 506, the cognitive load driving assistant 260 computes the current cognitive load 350 based on the driver-facing sensor data. At step 508, the cognitive load driving assistant 260 computes the current driving context 370 based on the non-driver-facing sensor data in conjunction with other relevant environmental and vehicle data. The additional data may include any type of data received in any technically feasible fashion. For example, and without limitation, the additional data could include a location of the vehicle based on data received via the GNSS receiver 236 and locations of other vehicles based on V2X data 238. As persons skilled in the art will recognize, the cognitive load driving assistant 260 typically performs steps 506 and steps 508 substantially in parallel.

At step 510, the cognitive load driving assistant 260 transmits the current cognitive load 350 and the current driving context 370 to the cognitive load database 282 included in the cloud 280. Sharing cognitive data in this manner enables other cognitive load driving assistants 260 included in other vehicles to alert other drivers when the current cognitive load 350 indicates that the driver of the vehicle may pose a safety risk.

At step 512, the cognitive load feedback engine 380 computes the baseline cognitive load 474 based on historical cognitive load data in conjunction with historical driving contexts. The historical cognitive load data and the historical driving contexts may be stored in any memory, in any technically feasible fashion, and include any amount of data associated with any number of drivers. For example, and without limitation, the historical cognitive load data could be stored in the cognitive load database 282 and include data for many drivers. The cognitive load feedback engine 380 may compute the baseline cognitive load 474 in any technically feasible fashion. For example, and without limitation, the cognitive load feedback engine 380 could compute the baseline cognitive load 474 as the average of all historical cognitive loads associated with the driver.

At step 514, the cognitive load feedback engine 380 compares the current cognitive load 350 to the baseline cognitive load 474. If, at step 514, the cognitive load feedback engine 380 determines that the current cognitive load 350 is not greater than the baseline cognitive load 474, then the method 500 returns to step 504 where the cognitive load driving assistant 260 receives new sensor data. If, however, at step 514, the cognitive load feedback engine 380 determines that the current cognitive load 350 is greater than the baseline cognitive load 474, then the method 500 proceeds directly to step 516.

At step 516, the cognitive load feedback engine 380 provides feedback to the driver indicating the elevated current cognitive load 350. The cognitive load feedback engine 380 may provide the feedback in any technically feasible fashion and may include any additional data for reference. For example, and without limitation, the cognitive load feedback engine 380 could display an "evaluated cognitive load" warning via the dashboard-mounted display device 214. The warning could include the current cognitive load 350 and an indication of how the current cognitive load 350 relates to the baseline cognitive load 474. In another example, and without limitation, the cognitive load feedback engine 380 could audibly warn the driver that the current cognitive load 350 indicates a dangerous driving situation.

At step 518, the cognitive load feedback engine 380 performs corrective actions designed to reduce the driving task load 450 and/or the secondary task load 460 based on the current driving context 370 and/or the historical driving contexts. For example, and without limitation, the cognitive load feedback engine 380 could determine that the current driving route is challenging and, in response, interact with the navigation subsystem 246 to suggest a less congested route for the vehicle. In another example, and without limitation, the cognitive load feedback engine 380 could determine that the number of secondary tasks that the driver is performing significantly exceeds the number of secondary tasks that the driver typically performs and, in response, interact with the entertainment subsystem 244 to mute the speakers.

The method 500 then returns to step 504 where the cognitive load driving assistant 260 receives new sensor data. The cognitive load driving assistant 260 continues to cycle through steps 504-518, assessing the current cognitive load 350 to detect and attempt to minimize situations associated with elevated cognitive loads until the vehicle or the cognitive load driving assistant 260 is turned off.

In one embodiment, a cognitive driving assistant analyzes driver-facing sensor data and provides feedback regarding elevated driver cognitive loads to enable drivers to recognize and react to dangerous driving environments. In operation, the cognitive driving assistant processes driver-facing sensor data to compute a current cognitive load. Substantially in parallel, the cognitive driving assistant processes non driver-facing sensor data along with other relevant data, such as GNSS data, to generate a current driving context. The current driving context includes driving parameters, vehicle parameters, environmental parameters, and secondary task parameters.

Because the impacts of different "distractions," such as talking on a cellular phone, vary between individual drivers, a cognitive load feedback engine analyzes the current cognitive load of the driver with respect to historical cognitive loads of the driver in similar driving contexts. For example, if a current time included in the current driving context indicates night time lighting conditions, then the cognitive load feedback engine could compare the current cognitive load of the driver to historical cognitive loads in other driving contexts that indicate night time lighting conditions. If the cognitive load feedback engine determines that the current cognitive load is greater than the "baseline" cognitive load in similar driving contexts, then the cognitive load feedback engine initiates corrective action. The corrective action may include any type of passive feedback, such as an audible warning, or any type of active control, such as disabling a ringer of a cellular phone.

In some embodiments, the cognitive load feedback engine transmits the current cognitive load and/or the current driving context to a cognitive load database stored in a public cloud. Such information enables other cognitive load feedback engines operating in other vehicles to preemptively identify dangerous driving situations. For example, if the current cognitive load of the driver is elevated, then a cognitive load feedback engine in a second vehicle located in the immediate vicinity of the vehicle could notify the driver of the second vehicle that a distracted driver is nearby.

At least one advantage of the disclosed approach is that because the cognitive load feedback engine enables drivers to adjust driving and/or secondary task behavior based on cognitive loads, driver safety may be increased. In particular, educating drivers on their cognitive load levels and/or the cognitive load levels of nearby drivers provides drivers with an opportunity to increase their concentration on the primary driving task during challenging driving situations and/or reduce their concentration on secondary tasks. Consequently, driver safety may be increased for the driver as well as nearby drivers.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. One or more non-transitory computer-readable storage media including instructions that, when executed by one or more processors, cause the one or more processors to perform the steps of:
   computing a current cognitive load associated with a driver while the driver is operating a vehicle based on data received via one or more sensors;
   computing a confidence factor associated with the current cognitive load based on data received via one or more other sensors;
   computing a threshold cognitive load;
   determining that the current cognitive load exceeds the threshold cognitive load; and
   in response, causing one or more actions to occur that are intended to reduce the current cognitive load associated with the driver.

2. The one or more computer-readable storage media of claim 1, wherein causing one or more actions to occur comprises configuring a display screen to display the current cognitive load.

3. The one or more computer-readable storage media of claim 1, wherein causing one or more actions to occur comprises configuring an entertainment subsystem to reduce the volume of an audio signal.

4. The one or more computer-readable storage media of claim 1, wherein causing one or more actions to occur comprises causing a navigation subsystem to generate a modified driving route that has less cognitive complexity than a current driving route.

5. The one or more computer-readable storage media of claim 1, wherein the one or more sensors measure one or more physiological changes in a body of the driver.

6. The one or more computer-readable storage media of claim 5, wherein the one or more physiological changes are associated with at least one of a brain activity, a heart rate, a skin conductance, and sizes of pupils.

7. The one or more computer-readable storage media of claim 5, wherein computing the current cognitive load comprises:
   performing a multiplication operation between a first measurement received via a first sensor included in the one or more sensors and a first weight to generate a first weighted measurement;

performing a multiplication operation between a second measurement received via a second sensor included in the one or more sensors and a second weight to generate a second weighted measurement; and computing an average of the first weighted measurement and the second weighted measurement.

8. The one or more computer-readable storage media of claim 1, wherein at least one or the one or more sensors measures sizes of pupils and the one or more other sensors measure at least one of a brain activity, a heart rate, and a skin conductance.

9. The one or more computer-readable storage media of claim 1, further comprising computing the threshold cognitive load based on a plurality of previous cognitive loads computed for the driver.

10. The one or more computer-readable storage media of claim 1, further comprising computing the threshold cognitive load based on a plurality of current cognitive loads computed for a plurality of other drivers.

11. A method for sharing cognitive load while driving, the method comprising:

computing a first cognitive load of a first driver based on data received via one or more sensors, wherein the first driver and the one or more sensors are associated with a first vehicle;

sharing the first cognitive load with a second driver that is associated with a second vehicle;

receiving a second cognitive load that is associated with the second driver; and in response to receiving the second cognitive load, modifying a characteristic of the first vehicle.

12. The method of claim 11, wherein sharing the first cognitive load comprises storing the first cognitive load in a cognitive load database included in a cloud that is accessible to the second vehicle.

13. The method of claim 11, wherein sharing the first cognitive load comprises transmitting vehicle-to-everything data that includes the first cognitive load to the second vehicle.

14. A system configured to manage cognitive load while driving, the system comprising:

a memory storing a cognitive load driving assistant; and a processor that is coupled to the memory and, when executing the cognitive load driving assistant, is configured to:

compute a current cognitive load associated with a driver, while the driver is operating a vehicle, based on data received via one or more sensors;

compute a confidence factor associated with the current cognitive load based on data received via one or more other sensors;

determine a threshold cognitive load;

determine that the current cognitive load exceeds the threshold cognitive load; and taking one or more actions that are intended to reduce the current cognitive load below the threshold cognitive load.

15. The system of claim 14, wherein taking one or more actions comprises configuring a display screen to display the current cognitive load.

16. The system of claim 14, wherein taking one or more actions comprises configuring an advanced driver assistance system (ADAS) to increase the conservatism of one or more safety features associated with the vehicle.

17. The system of claim 14, wherein the processor is further configured to:

compute a current driving context based on data received via one or more other sensors;

select a previous driving context from a cognitive load database based on the current driving context; and assign the threshold cognitive load based on a previous cognitive load associated with the previous driving context.

* * * * *